(12) United States Patent
Harder et al.

(10) Patent No.: US 8,784,431 B1
(45) Date of Patent: Jul. 22, 2014

(54) MEDICAL SCREWDRIVER

(75) Inventors: Benjamin G. Harder, Knoxville, TN (US); Michael J. Brow, Knoxville, TN (US)

(73) Assignee: Choice Spine, LP, Knoxville, TN (US)

( * ) Notice: Subject to any disclaimer, the term of this patent is extended or adjusted under 35 U.S.C. 154(b) by 137 days.

(21) Appl. No.: 13/493,007

(22) Filed: Jun. 11, 2012

(51) Int. Cl.
*A61B 17/88* (2006.01)

(52) U.S. Cl.
USPC .................. 606/104; 606/99; 606/86 A (58) Field of Classification Search
CPC ........... A61B 17/7082; A61B 17/8886; A61B 17/8888; A61B 17/8891
USPC ......... 606/99, 104, 86 A, 915, 916; 81/177.2, 81/451; 403/104–107, 348, 376, 377, 403/379.5
See application file for complete search history.

(56) References Cited

U.S. PATENT DOCUMENTS

| | | | |
|---|---|---|---|
| 5,156,064 A * | 10/1992 | Truman .................. | 74/501.5 R |
| 5,946,988 A | 9/1999 | Metz-Stavehagen | |
| 5,988,337 A * | 11/1999 | Liu .............................. | 192/43.1 |
| 5,996,452 A * | 12/1999 | Chiang .......................... | 81/429 |
| 6,575,974 B2 * | 6/2003 | Gotfried ......................... | 606/67 |
| 6,701,812 B1 * | 3/2004 | Sawamura ..................... | 81/453 |
| 6,723,100 B2 * | 4/2004 | Biedermann et al. ......... | 606/308 |
| 7,181,997 B1 * | 2/2007 | Rinner et al. .................. | 81/58.4 |
| 7,226,453 B2 | 6/2007 | Chao et al. | |
| 7,367,979 B2 | 5/2008 | Abdelgany | |
| 7,517,179 B2 * | 4/2009 | Miller et al. .................. | 408/204 |
| 7,559,930 B2 * | 7/2009 | Allard et al. ............... | 606/86 A |
| 7,575,581 B2 | 8/2009 | Lovell | |
| 7,743,684 B2 * | 6/2010 | Guile et al. ..................... | 81/125 |
| 7,985,242 B2 | 7/2011 | Forton et al. | |
| 8,016,836 B2 | 9/2011 | Corrao et al. | |
| 8,051,751 B2 * | 11/2011 | Huang .............................. | 81/475 |
| 8,100,916 B2 * | 1/2012 | Kumar et al. .................. | 606/104 |
| 8,161,849 B2 * | 4/2012 | Stark ............................... | 81/473 |
| 8,162,952 B2 * | 4/2012 | Cohen et al. ................... | 606/104 |
| 8,172,847 B2 * | 5/2012 | Dziedzic et al. ............ | 606/86 A |
| 8,257,004 B2 * | 9/2012 | Smith ............................. | 411/265 |
| 8,545,505 B2 * | 10/2013 | Sandstrom et al. ......... | 606/86 A |
| 8,551,141 B2 * | 10/2013 | Gephart et al. ............... | 606/246 |
| 2008/0200918 A1 | 8/2008 | Spitler et al. | |
| 2008/0221583 A1 | 9/2008 | Sharifi-Mehr et al. | |
| 2008/0243134 A1 * | 10/2008 | Limberg et al. ............... | 606/104 |
| 2009/0180830 A1 * | 7/2009 | MacLean ....................... | 403/348 |
| 2009/0275954 A1 * | 11/2009 | Phan et al. ..................... | 606/104 |
| 2010/0298838 A1 | 11/2010 | Walters | |

* cited by examiner

*Primary Examiner* — Michael T Schaper
*Assistant Examiner* — Amy Sipp
(74) *Attorney, Agent, or Firm* — Luedeka Neely Group, PC (57) ABSTRACT

A medical screwdriver configured to avoid disengaging from a screw during implantation of the screw at a surgical site, the screwdriver including an outer shaft having a housing in which is located a piston and a spring, an inner shaft, and a collar. When the collar is rotated in a first direction the collar is positioned at a first position and the inner shaft is rotationally coupled to the outer shaft. When the collar is rotated in a second direction opposite the first direction, the collar moves to a second position and the inner shaft is unlocked from the outer shaft.

4 Claims, 13 Drawing Sheets

MEDICAL SCREWDRIVER

FIELD

This disclosure relates to the field of medical screwdrivers. More particularly, the disclosure relates to a medical screwdriver configured to avoid disengaging prematurely before a screw is properly installed at the surgical site.

BACKGROUND

Medical screwdrivers of the type used to install pedicle screws typically have an inner portion that can be driven to install a screw and an outer portion to engage the screw during installation.

One problem associated with conventional screwdrivers is that the screwdriver can often at least partially disengage from a screw, such as a pedicle screw, during installation of a screw.

Accordingly, what is desired is an improved screwdriver structure that avoids disengagement from the screw during installation of the screw at the surgical site.

The disclosure relates to an improved screwdriver structure that enables selective engagement and disengagement of an inner shaft and an outer shaft of the screwdriver. The shafts are engaged for installation of a screw, then disengaged to allow the inner shaft to rotate freely from the outer shaft and disengage from the screw so that the screw does not disengage prematurely before it is properly installed at the surgical site.

SUMMARY

The disclosure relates to a medical screwdriver configured to avoid disengaging prematurely before the screw is properly installed at the surgical site.

In one aspect, the screwdriver includes an outer shaft having a housing in which is located a piston and a spring, an inner shaft, and a collar.

The outer shaft includes a first end, a housing defined at an opposite second end of the outer shaft, and a central bore extending through the length of the outer shaft. The housing includes a cavity located to intersect the central bore; a spring positioned within the cavity; and a piston positioned within the cavity of the housing of the outer shaft. The piston has an end extending outwardly of the cavity, an opposite base in contact with the spring, and a bore extending through the piston, the bore including an interior projection.

The inner shaft has a first end, an opposite second end, and a toothed circumferential surface located between the ends of the shaft. The inner shaft is positioned within the central bore of the outer shaft and passes through the bore of the piston and is located so that the toothed surface of the inner shaft is proximate the bore of the piston for permitting selective engagement of the interior projection of the piston with the toothed surface of the inner shaft.

The collar is rotatably positioned on the housing of the outer shaft and is rotatable between a first position and a second position. The collar includes a sidewall and an interior profiled cam located along an interior portion of the sidewall. The cam includes first and second cam surfaces.

When the collar is rotated in a first direction, such as clockwise, the collar moves to the first position with the first cam surface adjacent the piston. The first cam surface allows sufficient clearance for the spring and piston to translate. The spring forces the interior projection of the piston to engage with the toothed circumferential surface of the inner shaft. As the collar is further rotated in the first direction, the outer shaft is engaged and rotates in the first direction along with the collar and the outer shaft engages with the surgical screw. As the collar and outer shaft rotate in the first direction the piston indexes to a subsequent tooth of the shaft as the spring ensures it remains in contact with the circumferential teeth of the inner shaft. Once the outer shaft is sufficiently tightened to the surgical screw, the piston remains locked to the inner shaft until the surgical screw has been installed at the surgical site.

When the collar is rotated in the opposite direction, such as counterclockwise, the second cam surface contacts the piston and compresses the spring. The piston disengages from the inner shaft and unlocks the outer shaft from the inner shaft allowing removal of the screwdriver from the installed surgical screw.

BRIEF DESCRIPTION OF THE DRAWINGS

Further advantages of the disclosure are apparent by reference to the detailed description when considered in conjunction with the figures, which are not to scale so as to more clearly show the details, wherein like reference numbers indicate like elements throughout the several views, and wherein.

DETAILED DESCRIPTION

With reference to the drawings, the disclosure relates to a medical screwdriver 10 having a drive 12, a collar 14, a pin 16, a piston 18, a spring 20, an outer shaft 22, an inner shaft 24, an exterior sleeve 26, and a retaining ring 28. The screwdriver 10 is particularly configured for installing a pedicle screw 30 of the type having a polyaxial head 31 below a tulip-shaped head 32 having internal threads. In regards to the following description, it will be understood that the screw 30 is configured to have bone engaging threads 34 configured to tighten the screw 30 into the bone as the screw 30 is rotated clockwise. Accordingly, the screwdriver 10 is described herein with respect to installation of such screws.

As previously noted, one problem associated with conventional screwdrivers is that the screwdriver can often at least partially disengage from a screw during installation of the screw. The screwdriver 10 is configured to avoid disengaging prematurely before the screw is fully installed at the surgical site.

The drive 12 is configured to connect a handle or driver operated by a surgeon to the screwdriver 10 so that force can be transmitted to install a screw. In one embodiment, the drive 12 includes a square drive surface 36 at one end for connecting to a handle. The opposite end of the drive 12 defines a blind bore 38 having ridges defined around the inner periphery thereof. The bore 38 slips over an end of the inner shaft 24.

Figure 4:
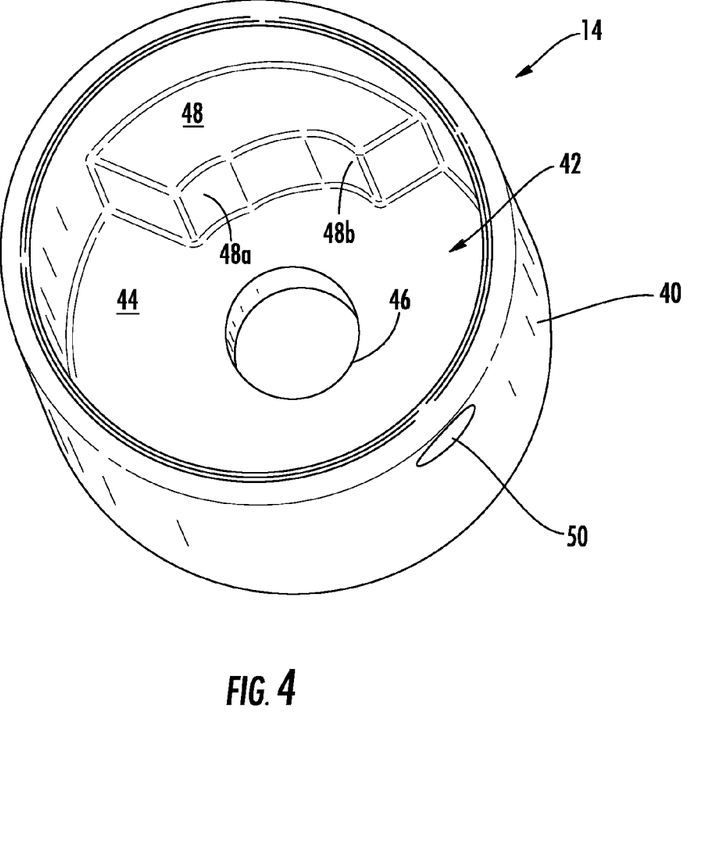
FIG. 4 shows a collar component of the screwdriver of FIG. 1.

The collar 14 includes a cylindrical sidewall 40 having an open end 42 and an opposite substantially closed end 44 having a central aperture 46. An interior profiled cam 48 is located along an interior portion of the sidewall 40 adjacent the closed end 44. The cam 48 includes cam surfaces 48a and 48b at opposite ends of the cam 48. As explained more fully below, when the collar 14 is rotated in a clockwise direction the cam surface 48a provides clearance room to permit the piston 18 to be positioned to lock the inner shaft 24 to the outer shaft 22. When the collar 14 is thereafter rotated in the opposite direction, the cam surface 48b positions the piston 18 to unlock the inner shaft 24 from the outer shaft 22.

The pin 16 is installed within an aperture 50 located on the collar 14 adjacent the open end 42. The pin 16 is oriented to extend into the open space of the interior of the collar 14. The pin 16 retains the collar 14 from dislocating or otherwise moving axially on the outer shaft 22.

Figure 5:
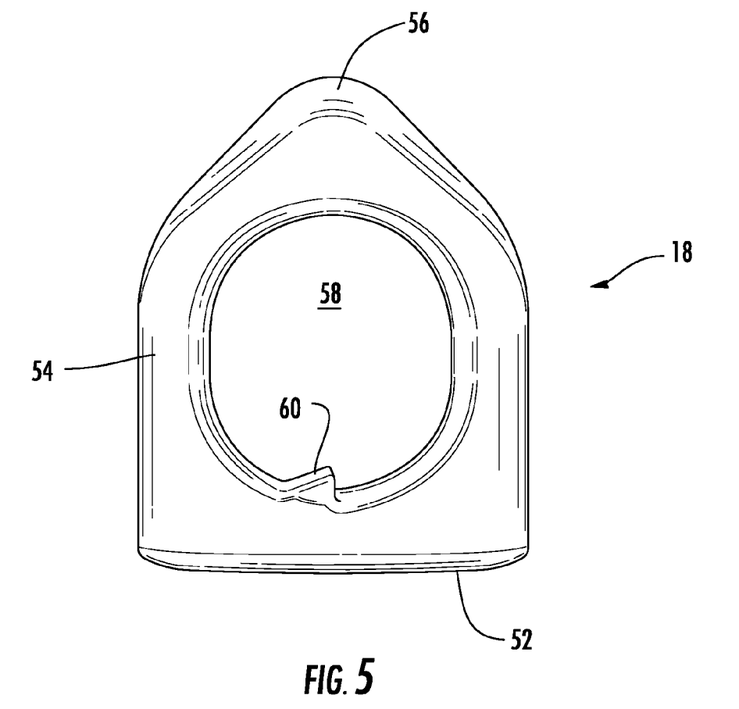
FIG. 5 shows a piston component of the screwdriver of FIG. 1.
Figure 6:
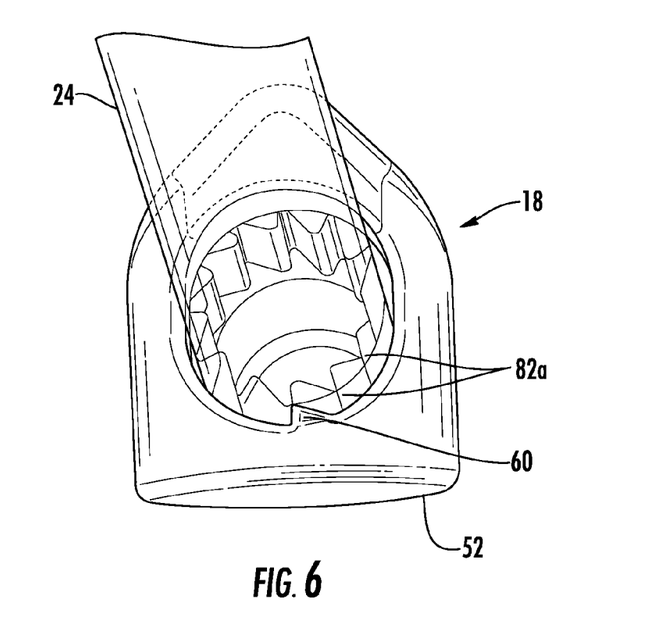
FIG. 6 shows the piston component of FIG. 5 located on an inner shaft component of the screwdriver of FIG. 1.

The piston 18 is shaped to include a substantially planar circular base 52, a cylindrical sidewall 54 extending from the base, and a pointed upper end 56. A bore 58 extends through the mid-section of the piston 18 to define opposite open ends through which the inner shaft 24 extends. The bore 58 includes a tooth or other interior projection 60 defined on a lower central portion of the bore 58.

The spring 20 is a compression type spring and may be provided as by a coil or wave spring. The use of a wave spring is preferred for reduced spring height. The spring 20 is provided to bear against the base 52 of the piston 18, as explained more fully below.

Figure 7:
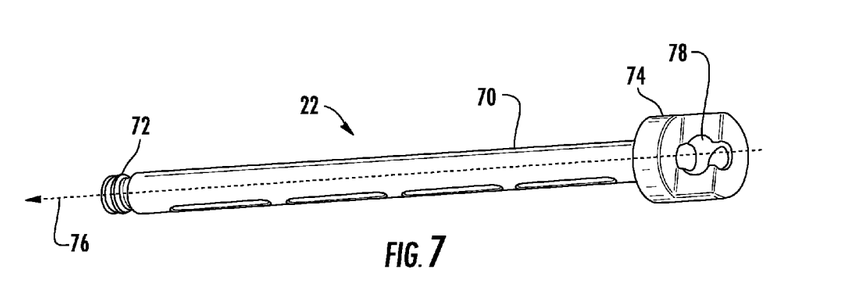
FIGS. 7 and 8 show an outer shaft component of the screwdriver of FIG. 1.
Figure 8:
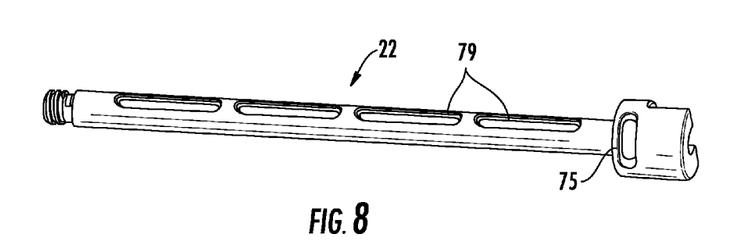

The outer shaft 22 includes an open-ended elongate slotted cylindrical member 70 having a threaded distal end 72 and a housing 74 defined at the opposite proximal end of the shaft 22 having stop surfaces 74a and 74b. A slot 75 is defined along a portion of the exterior of the housing 74 for receiving the pin 16. A central bore 76 extends through the length of the outer shaft 22 for receiving the inner shaft 24. The housing 74 includes a cavity 78 located perpendicular to the bore 76 and configured to receive the piston 18 and the spring 20. Slots 79 extend through the sidewall of the cylindrical member 70. The slots 79 are provided for facilitating sterilization and cleaning.

Figure 9:
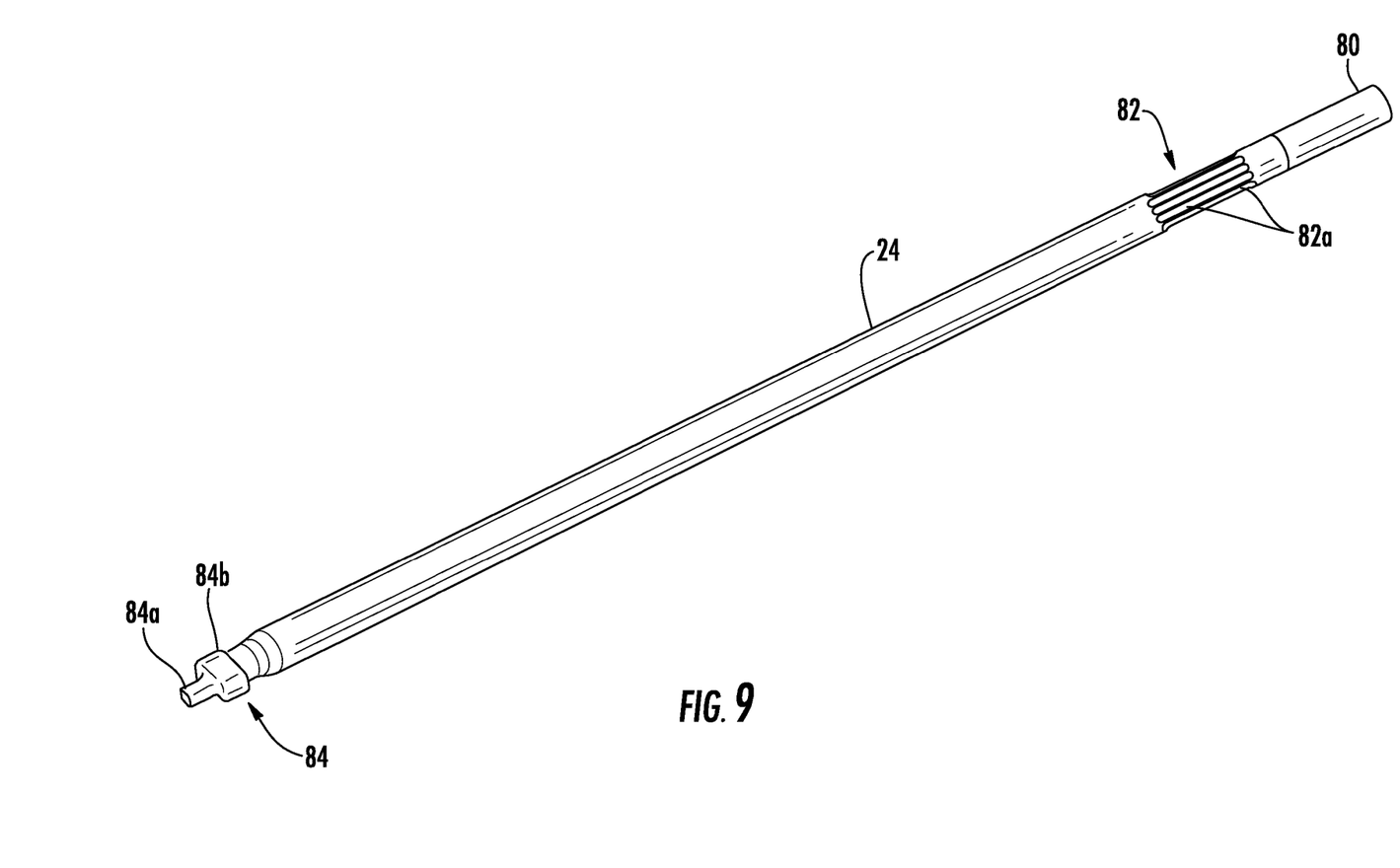
FIG. 9 shows an inner shaft component of the screwdriver of FIG. 1.
Figure 10:
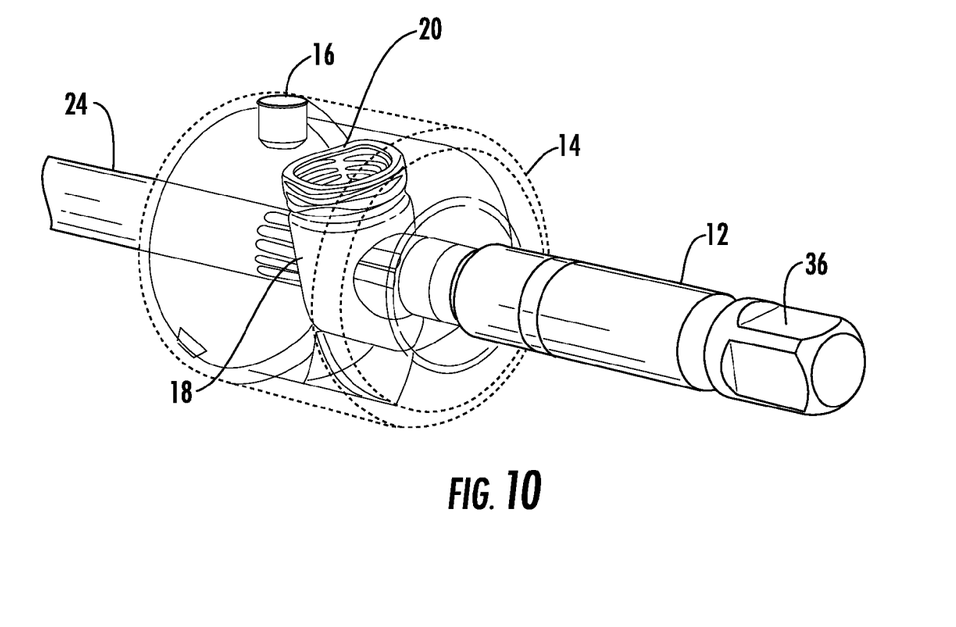
FIG. 10 and FIG. 11 show the piston component positioned within the collar component of the screwdriver of FIG. 1, with FIG. 10 showing the collar transparent.
Figure 11:
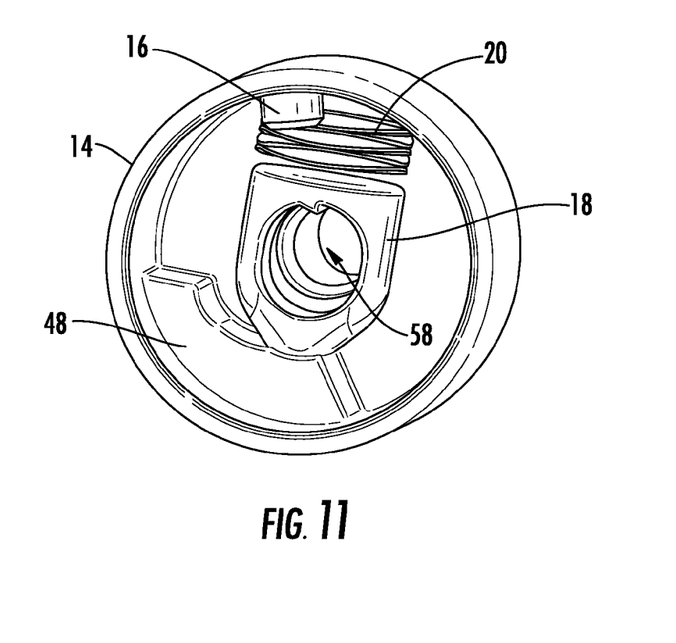
Figure 12:
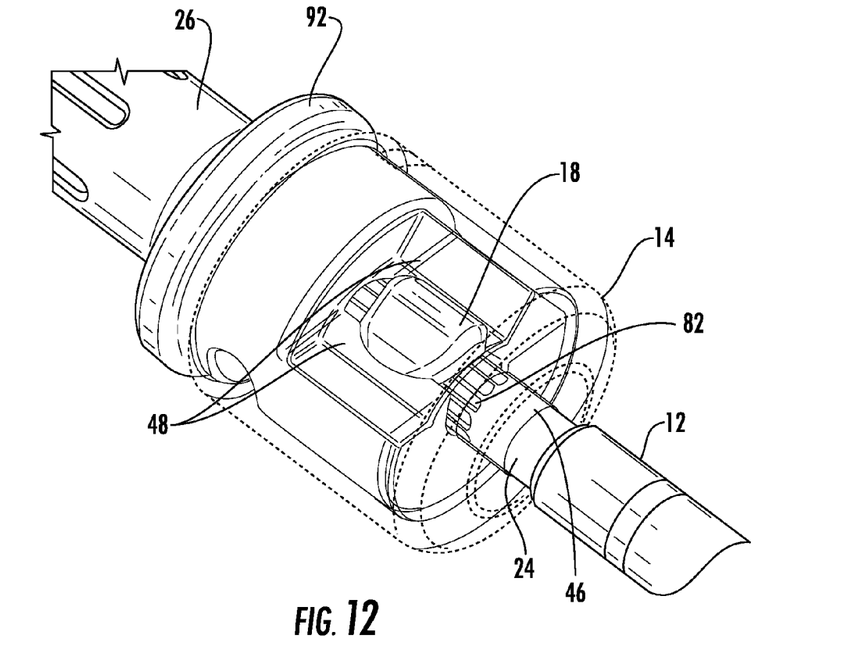
FIG. 12 is an assembled interior view with the collar transparent.

The inner shaft 24 has a proximal end 80 configured to receive the bore 32 of the drive 12. A peripheral toothed surface 82 defining a plurality of teeth 822 is located adjacent the proximal end 80. The teeth 82a are configured for engaging the interior projection 60 of the piston 18, as described more fully below. A distal end 84 of the inner shaft 24 is configured for engaging the pedicle screw 30. For example, the distal end 84 may include a drive tip 84a configured to drivingly engage a corresponding drive surface (such as a hex or slot) of the polyaxial head 31 of the screw 30 and a crosspiece 84b configured for being received by side slots of the tulip head 32

The exterior sleeve 26 includes an elongate slotted open-ended cylindrical member 90 having an exterior rim 92 defined on the proximal open end. The exterior sleeve 36 rotates independently from the outer shaft 22 and the inner shaft 24 and is configured so that a user may grasp for guidance of the screw during installation. The exterior rim 92 provides a hand stop used to avoid contact with the collar 14 during screw installation. A central bore extends through the length of the sleeve 26 for receiving the outer shaft 22. The retaining ring 28 fits onto the distal open end of the sleeve 26. For example, the ring 28 may have a slightly reduced diameter portion that fits within the end of the sleeve 26 to seat the retaining ring 28 onto the end of the sleeve 26 while still permitting the outer shaft 22 to pass through the end of the sleeve 26.

Figure 1:
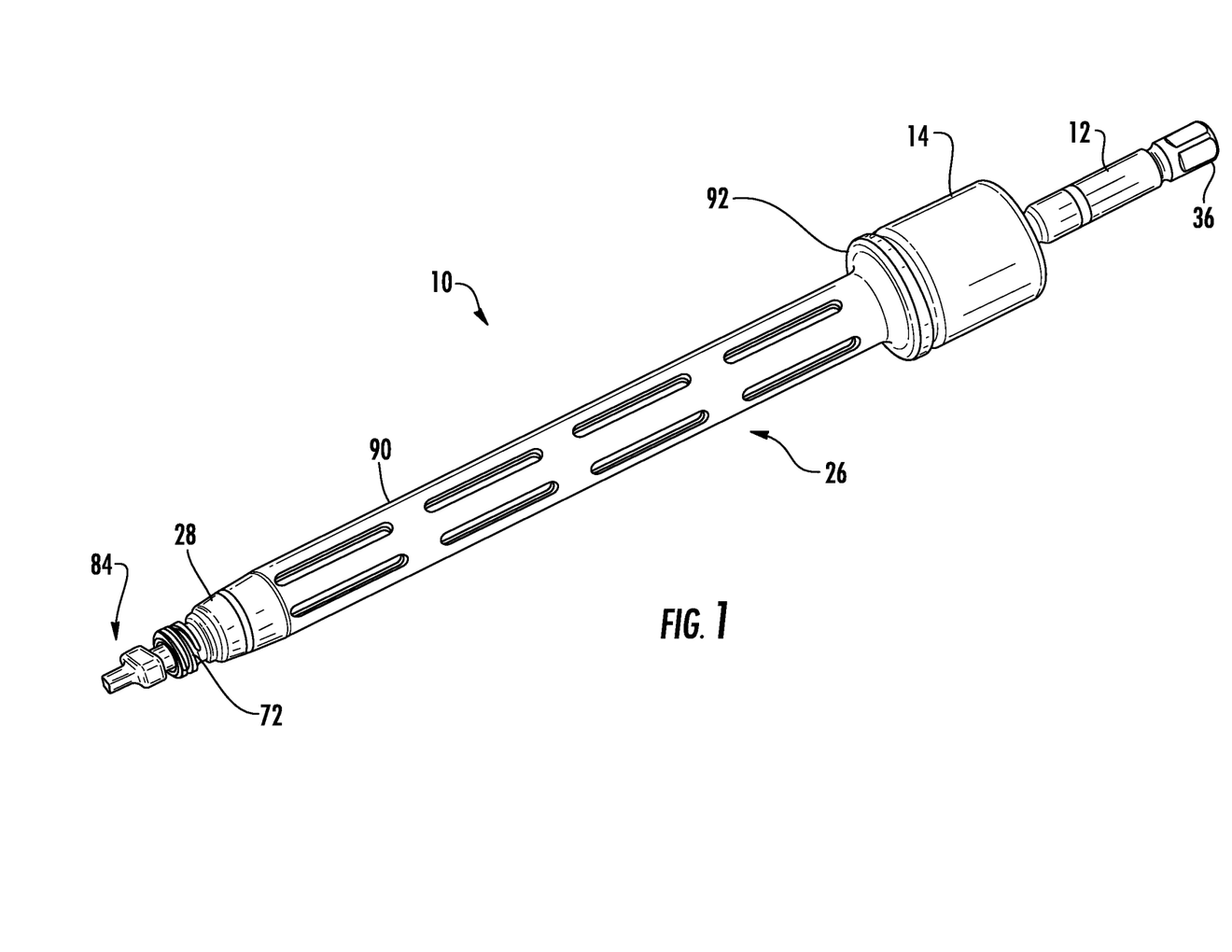
FIG. 1 is a perspective view of a medical screwdriver according to the disclosure.
Figure 2:
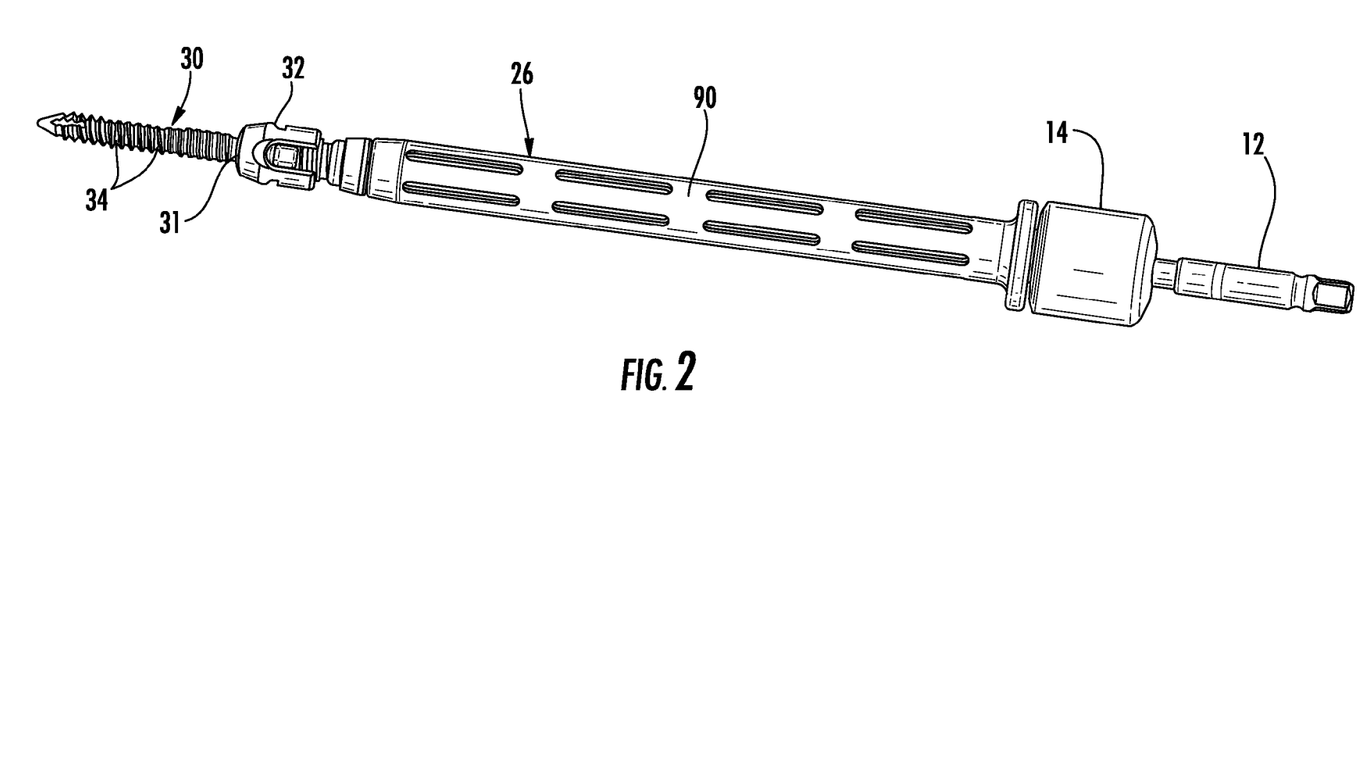
FIG. 2 shows the screwdriver of FIG. 1 engaged with a pedicle screw.
Figure 3:
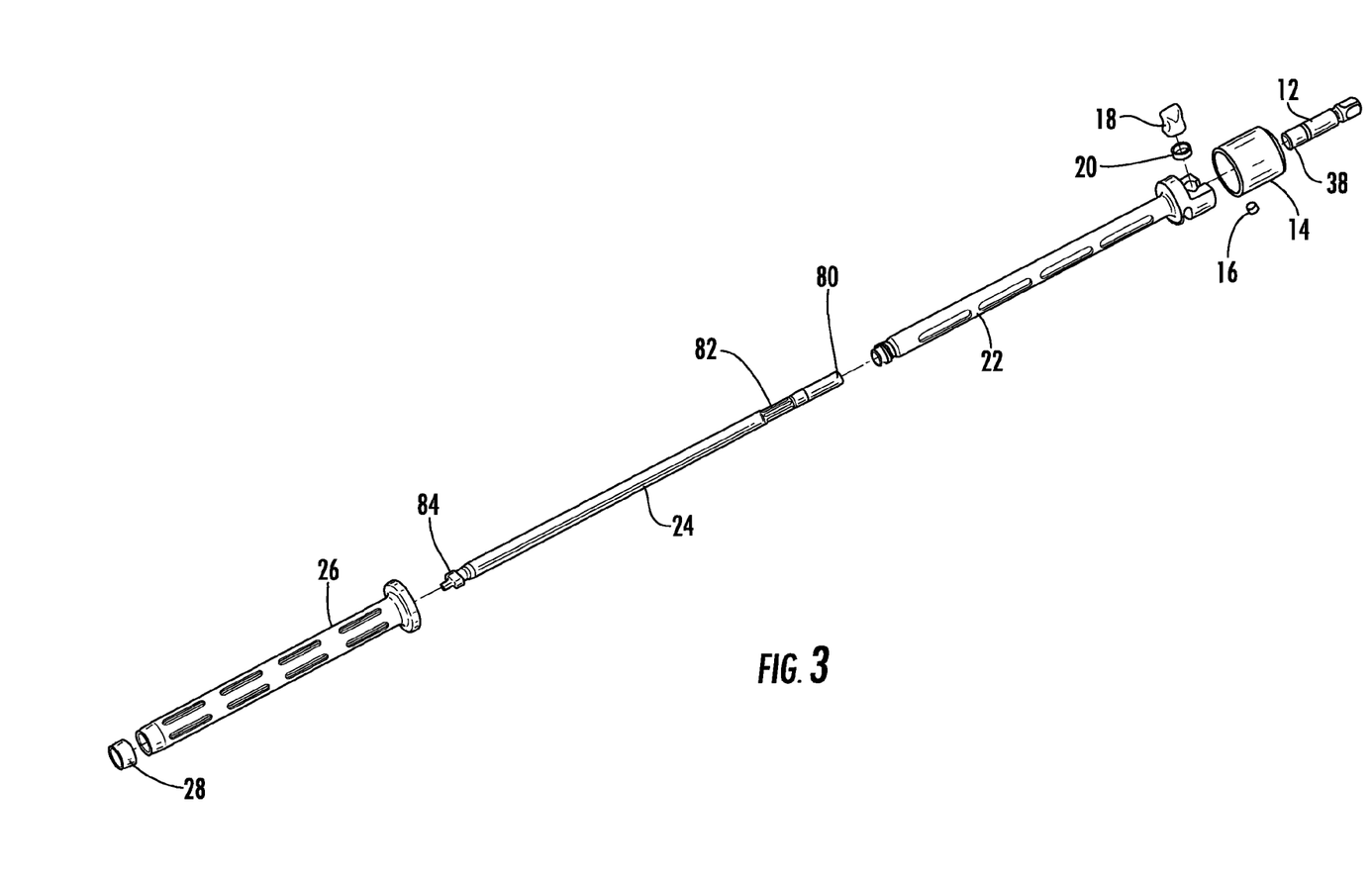
FIG. 3 is an exploded view of the screwdriver of FIG. 1.

With additional reference to FIGS. 10-17, in the assembled state of the screwdriver 10, the collar 14 fits over the housing 74 of the outer shaft 22, with the piston 18 and the spring 20 located within the cavity 78 of the housing 74. The inner shaft 24 extends through the aperture 46 of the collar 14 and the bore 76 of the outer shaft 22. The inner shaft 24 passes through the bore 58 of the piston 18 such that the piston 18, which is located in the cavity 78 of the housing 74 and biased by the spring 20, straddles the toothed surface 82 of the inner shaft 24 and the pointed upper end 56 of the piston 18 bears against the cam 48. The outer shaft 22 (having the inner shaft 24 therein) is received by the sleeve 26 such that the distal end 84 of the inner shaft 24 and the threaded distal end 72 of the outer shaft 22 extend out of the sleeve 26, as best seen in FIG. 1. The drive 12 is positioned on the proximal end of the inner shaft 24 adjacent the collar 14. The drive 12 may be connected to a handle or driver operated by a surgeon so that force can be transmitted to the screwdriver 10 to install the screw 30.

In use of the screwdriver 10, as the drive 12 is rotated clockwise to tighten and install the pedicle screw 30 into a bone at a surgical site, the surgeon will rotate the collar 14 clockwise to bear the cam 48 against the stop surface 74a of the housing 74 and to also engage the piston 18 with the inner shaft 24 and lock the inner shaft 24 to the outer shaft 22.

Figure 15:
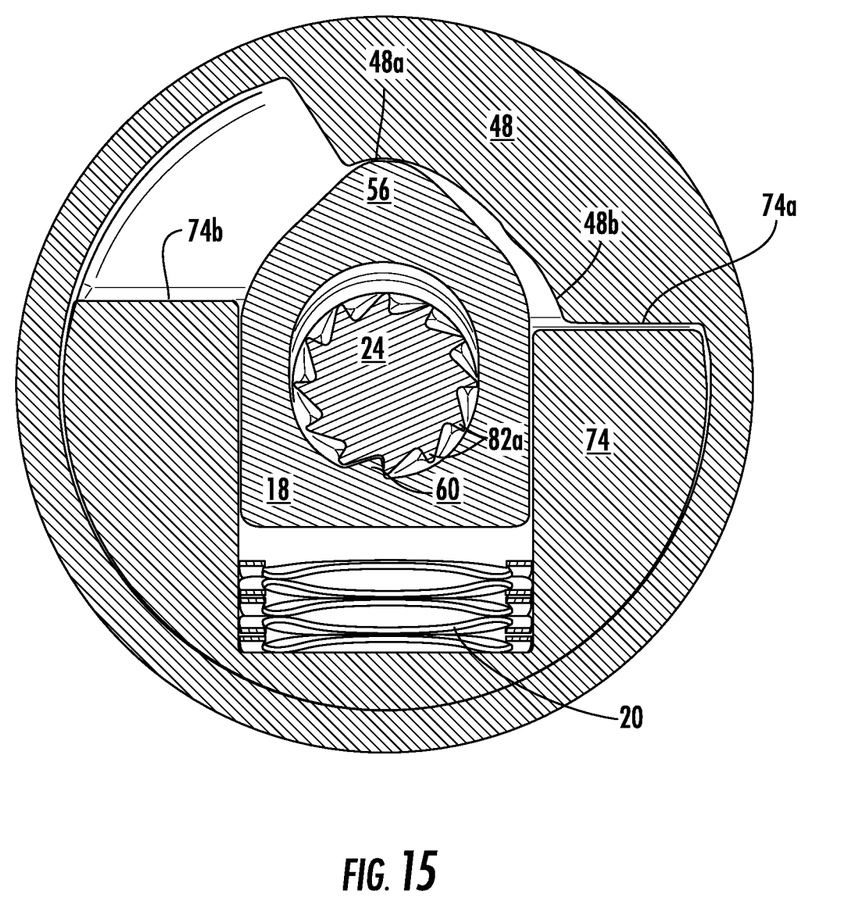
FIG. 15 is a cross-sectional view showing the positioning of the piston relative to the collar when the piston is engaged with the inner shaft.
Figure 16:
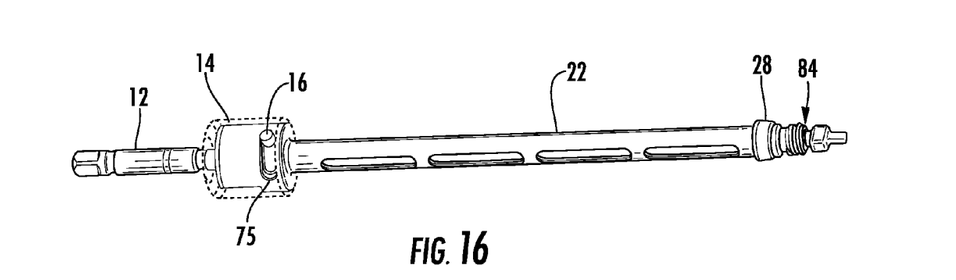
FIGS. 16 and 17 are partially assembled views of the screwdriver of FIG. 1.
Figure 17:
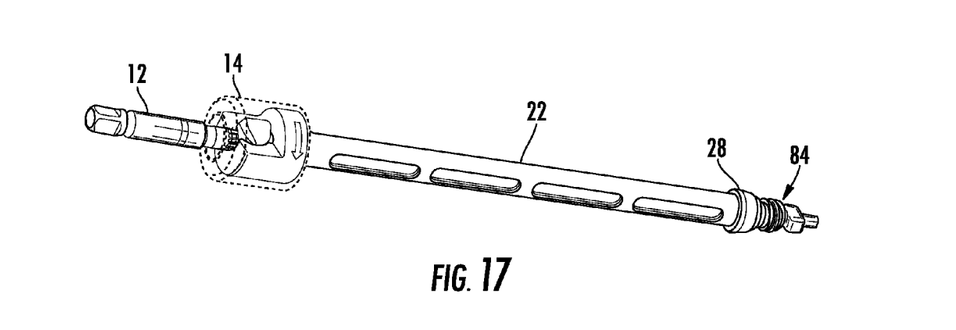

For example, as shown in FIG. 15, the cam surface 48a of the cam 48 provides the piston 18 sufficient clearance so that the piston 18 is located so that the interior projection 60 of the piston 18 engages one of the teeth 82a of the inner shaft 24. Thus, as the collar 14 is rotated clockwise, the cam 48 rotates to the lock position where the piston 18 bears against the surface 48a to position the piston 18 so that the interior projection 60 engages the teeth 82a on the inner shaft 24 of the screwdriver 10. As the collar 14 is rotated further in the clockwise direction, the interior projection 60 of the piston 18 will index to the next tooth 82a on the inner shaft 24 until the threaded end 72 of outer shaft 22 of the screwdriver 10 is fully tightened into the threads of the tulip shaped head 32 of the pedicle screw 30. Once the outer shaft 22 is sufficiently tightened to the surgical screw, the piston 18 remains locked to the inner shaft 18 until the surgical screw 30 has been installed at the surgical site. Rotation of the screwdriver 10 in the clockwise direction is continued until the screw 30 is desirably installed at the surgical site.

When the collar 14 is rotated in the opposite direction (counter-clockwise), the cam 48 bears against the stop surface 74b and the piston 18 disengages from the inner shaft 24 and unlocks the outer shaft 22 from the inner shaft 24 allowing removal of the screwdriver 10 from the installed surgical screw 30.

Figure 13:
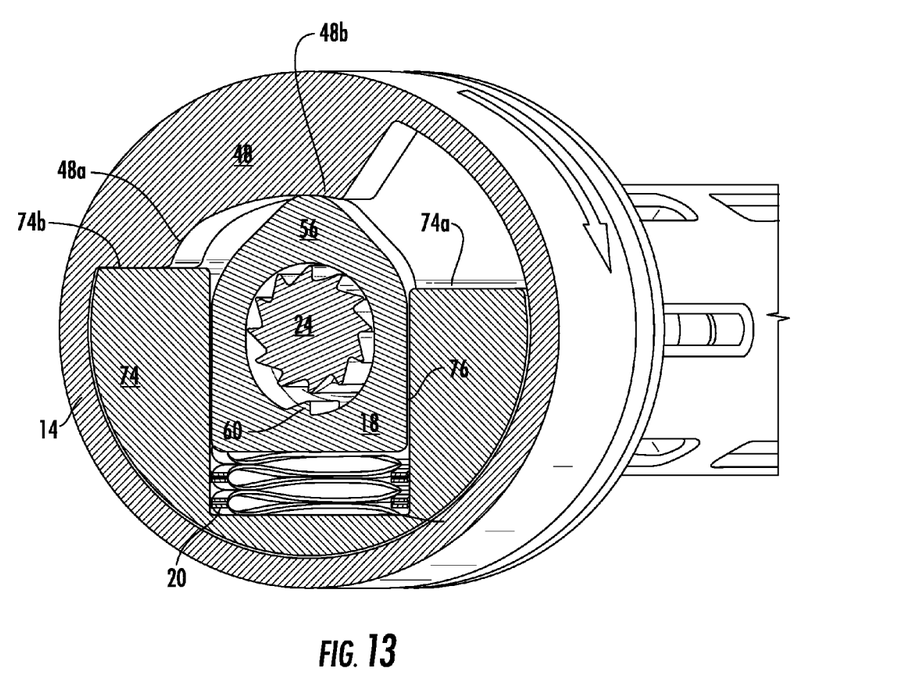
FIGS. 13 and 14 are cross-sectional views showing the positioning of the piston relative to the collar when the piston is disengaged from the inner shaft.
Figure 14:
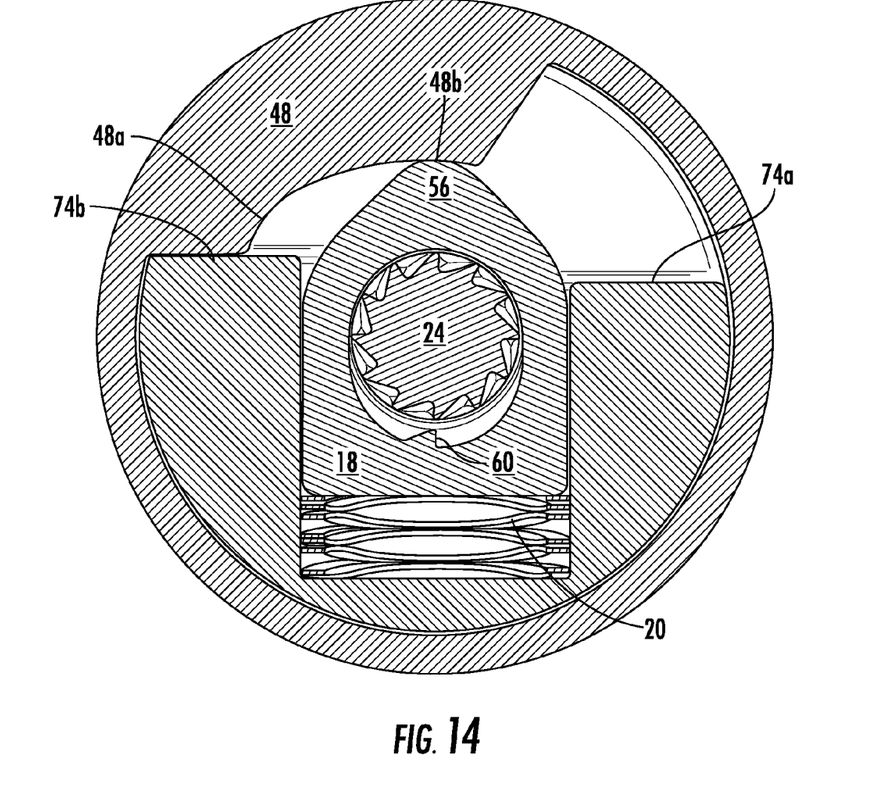

For example, as shown in FIGS. 13 and 14, the cam surface 48b urges the piston 18 away from the inner shaft 24 so that the interior projection 60 of the piston 18 does not engage any of the teeth 82a of the inner shaft 24. Thus, when the collar 14 is rotated counter-clockwise, the cam 48 rotates to an unlocked position, where the piston 18 bears against the surface 48b and is depressed and overcomes the force of the spring 12 so that the interior projection 60 on the piston 18 disengages from the teeth 82a on the inner shaft 24.

Accordingly, it will be appreciated that the configuration of the screwdriver 10 enables selective engagement and disengagement of the inner shaft 24 and the outer shaft 22 of the screwdriver 10. This enables threaded securement of the outer shaft 22 to the screw and, once the outer shaft is sufficiently tightened to the surgical screw, the piston remains locked to the inner shaft until the surgical screw has been installed at the surgical site. This avoids premature disengagement of the screwdriver from the screw during installation. After the screw is installed, the collar 14 is rotated counterclockwise to bear the cam 48 against the stop surface 74b of the housing 74 and the inner shaft 24 is disengaged from the outer shaft 22 to allow removal of the screwdriver 10 from the installed surgical screw 30.

The foregoing description of preferred embodiments for this disclosure has been presented for purposes of illustration and description. It is not intended to be exhaustive or to limit the disclosure to the precise form disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the disclosure in various embodiments and with various modifications as are suited to the particular use contemplated. All such modifications and variations are within the scope of the disclosure as determined by the appended claims when interpreted in accordance with the breadth to which they are fairly, legally, and equitably entitled.

The invention claimed is:

1. A medical screwdriver configured to avoid disengaging from a screw during implantation of the screw at a surgical site, the screwdriver comprising:
   an outer shaft having a distal end configured to engage a head of the screw, a housing defined at an opposite proximal end of the shaft, and a central bore extending through the length of the outer shaft, the housing including a cavity located to intersect the central bore;
   a spring positioned within the cavity;
   a piston positioned within the cavity of the housing of the outer shaft, the piston having an end extending outwardly of the cavity, an opposite base in contact with the spring, and a bore extending through the piston, the bore including an interior projection;
   an inner shaft having a distal end configured for drivingly engaging a corresponding drive surface of the screw, an opposite proximal end, and a toothed circumferential surface located between the ends of the shaft, the inner shaft being positioned within the central bore of the outer shaft and passing through the bore of the piston and located so that the toothed surface of the inner shaft is proximate the bore of the piston for permitting selective engagement of the interior projection of the piston with the toothed surface of the inner shaft; and
   a collar rotatably positioned on the housing of the outer shalt and rotatable between a first position and a second position, the collar including a sidewall and an interior profiled cam located along an interior portion of the sidewall, the cam including first and second cam surfaces;
   wherein, when the collar is rotated in a first direction the collar is positioned at the first position with the first cam surface adjacent the piston and the first cam surface provides sufficient clearance for the piston so that the piston is positioned with the interior projection of the piston in engagement with the toothed circumferential surface of the inner shaft and the spring forces the piston to maintain such engagement of the piston and the inner shaft so that the inner shaft is rotationally coupled to the outer shaft, and wherein when the collar is rotated in a second direction opposite the first direction, the collar is positioned at the second position and the piston is engaged by the second cam surface of the collar to overcome force supplied by the spring and position the piston so that the interior projection of the piston is disengaged from the toothed circumferential surface of the inner shaft and the inner shaft is not rotationally coupled to the outer shaft.

2. The screwdriver of claim 1, further comprising an exterior sleeve surrounding a portion of the outer shaft.

3. The screwdriver of claim 1, wherein the head of the screw is tulip-shaped and includes internal threads and the outer shaft includes a threaded end configured to threadably engage the threads of the tulip-shaped head.

4. The screwdriver of claim 1, wherein the outer shaft includes a pair of stop surfaces, one of which is contacted by the collar to transfer rotation of the collar in the first direction to the outer shaft, and the other of one of which is contacted by the collar to transfer rotation of the collar in the second direction to the outer shaft.

* * * * *